(12) United States Patent
Song et al.

(10) Patent No.: US 11,379,039 B2
(45) Date of Patent: Jul. 5, 2022

(54) BRAIN-COMPUTER INTERFACE METHOD AND SYSTEM BASED ON REAL-TIME CLOSED LOOP VIBRATION STIMULATION ENHANCEMENT

(71) Applicant: SOUTHEAST UNIVERSITY, Jiangsu (CN)

(72) Inventors: Aiguo Song, Jiangsu (CN); Wenbin Zhang, Jiangsu (CN); Hong Zeng, Jiangsu (CN); Baoguo Xu, Jiangsu (CN)

(73) Assignee: SOUTHEAST UNIVERSITY, Jiangsu (CN)

( * ) Notice: Subject to any disclaimer, the term of this patent is extended or adjusted under 35 U.S.C. 154(b) by 98 days.

(21) Appl. No.: 16/977,751

(22) PCT Filed: Mar. 21, 2019

(86) PCT No.: PCT/CN2019/079096
§ 371 (c)(1),
(2) Date: Sep. 2, 2020

(87) PCT Pub. No.: WO2020/124838
PCT Pub. Date: Jun. 25, 2020

(65) Prior Publication Data
US 2020/0401226 A1    Dec. 24, 2020

(30) Foreign Application Priority Data
Dec. 19, 2018  (CN) .......................... 201811553136.X

(51) Int. Cl.
*G06F 3/01* (2006.01)
*G06F 17/14* (2006.01)
(Continued)

(52) U.S. Cl.
CPC .............. *G06F 3/015* (2013.01); *A61B 5/316* (2021.01); *A61B 5/375* (2021.01); *A61B 5/378* (2021.01);
(Continued)

(58) Field of Classification Search
CPC .... G06F 3/015; G06F 3/016; G06F 2203/011; G06F 17/14; G06F 17/142; A61B 5/369;
(Continued)

(56) References Cited

U.S. PATENT DOCUMENTS

| 10,898,706 B2 * | 1/2021 | Pradeep ................ A61N 1/0534 |
| 2010/0042011 A1 * | 2/2010 | Doidge .................... G06T 17/10 |
| | | 600/544 |

(Continued)

FOREIGN PATENT DOCUMENTS

| CN | 103268149 A | 8/2013 |
| CN | 104951082 A | 9/2015 |

*Primary Examiner* — Dong Hui Liang
(74) *Attorney, Agent, or Firm* — Muncy, Geissler, Olds & Lowe, P.C.

(57) ABSTRACT

Brain-computer interface method and system include displaying and providing a motor imagery task to a subject, and collecting a generated digital electroencephalogram signal; reading the digital electroencephalogram signal, performing interception if a preset time period is exceeded, and performing continuous reading if not; performing band-pass filtering, obtaining time-frequency characteristics of the digital electroencephalogram signal, and extracting a frequency value with highest frequency energy as a main frequency; obtaining an instantaneous phase of the digital electroencephalogram signal; generating predicted sine waves by respectively using the main frequency and the instantaneous phase as a frequency and an initial phase of sine waves, and predicting and obtaining real-time phase information; and judging whether the real-time phase is in a vibration stimulation application phase interval, generating
(Continued)

and outputting a control instruction, and controlling a vibration motor to vibrate and to stimulate a sensory channel of the subject according to the control instruction.

10 Claims, 2 Drawing Sheets

(51) Int. Cl.
| | | |
|---|---|---|
| *A61B 5/375* | (2021.01) | |
| *A61B 5/377* | (2021.01) | |
| *A61B 5/24* | (2021.01) | |
| *A61B 5/00* | (2006.01) | |
| *A61B 5/378* | (2021.01) | |
| *A61B 5/316* | (2021.01) | |

(52) U.S. Cl.
CPC ............ *A61B 5/7455* (2013.01); *G06F 3/016* (2013.01); *G06F 17/142* (2013.01); *G06F 2203/011* (2013.01)

(58) Field of Classification Search
CPC ....... A61B 5/0006; A61B 5/374; A61B 5/375; A61B 5/6814; A61B 5/24; A61B 5/7455
See application file for complete search history.

(56) References Cited

U.S. PATENT DOCUMENTS

| | | | |
|---|---|---|---|
| 2014/0223462 A1* | 8/2014 | Aimone | ................... G06F 3/015 725/10 |
| 2019/0082990 A1* | 3/2019 | Poltorak | .............. A61B 5/7267 |

\* cited by examiner

BRAIN-COMPUTER INTERFACE METHOD AND SYSTEM BASED ON REAL-TIME CLOSED LOOP VIBRATION STIMULATION ENHANCEMENT

BACKGROUND

Technical Field

The present invention relates to a brain-computer interface method and system based on real-time closed loop vibration stimulation enhancement, and belongs to the technical field of a brain-computer interface.

Related Art

The first International Conference on Brain-Computer Interface held in 1999 gave the definition of a brain-computer interface, that is, the brain-computer interface is a communication system which does not depend on a normal output pathway consisting of peripheral nerves and muscles. A biological principle of the brain-computer interface is that when the brain performs thinking activities, generates motion consciousness or is stimulated by the outside, nerve cells will generate micro-electrical activities of dozens of millivolts, and the electrical activities of a large number of nerve cells are transmitted to the surface layer of the scalp to form brain waves. The brain-computer interface (BCI) is an advanced technology for converting brain activity features into predefined commands to thus realize communication with the outside or the control on other external devices on the basis of electroencephalogram signals or other related technologies.

Electroencephalogram signals extracted by a method of placing electrodes on the scalp are called as scalp electroencephalogram (EEG) signals. Because of isolation by meninges, skulls and multilayer tissues from the brain to the scalp, a signal-to-noise ratio of the EEG signals is very low, and it is difficult to extract stable and reliable signals. This is a serious problem in the control of external devices, and seriously influences the application range of the brain-computer interface. At the same time, there are differences between the EEG signals of different individuals. Studies show that a decoding rate is low in a process of using the brain-computer interface by about 30% of people, so that it is difficult to realize communication and control between the brain and the external environment. We call this kind of people as "BCI blind". Therefore, how to improve the practical performance of the decoding rate of BCI and the like is a key problem of the brain-computer interface.

BCI users can initiate brain control by simply executing imagery of left-hand or right-hand motions. The kinesthetic imagery of the hand motion generates event-related desynchronization/event-related synchronization (ERD/ERS) in the sensory motor cortex of the subject. The event-related synchronization is defined as a decrease or increase of power in a specific frequency band (such as α wave band 8-13 Hz). Generally, motor imagery-induced ERD activity focuses the contralateral hemisphere, that is, the motor imagery induces the ERD in the contralateral sensory motor cortex, and these lateral cortex activities constitute the neurophysiological basis of the motor imagery-based brain-computer interface.

A potential method to the problems faced by BCI development is to use the tactile sense. Tactile sensations produce less visual fatigue than visual stimulation, so that the user cannot generate excessive fatigue. The human tactile receptors are mainly Meissner corpuscles, distributed in the superficial skin and sensing the light pressing stimulation of the skin; Meissner's corpuscles, mainly responsible for sensing the tactile sensations; Pacinian corpuscles in a deeper layer, mainly sensing pressing sensations; and Pinkusi corpuscles, many nerve endings, tactile menisci, etc. The Meissner corpuscles are positioned at a tip adjacent to the main ridge and closest to the skin surface. They are very effective in signal conduction of low-frequency vibration (1-40 Hz), and thus achieve an important effect in sensory vibration detection.

More and more studies have shown that non-invasive electrical stimulation can more effectively modulate the neural activities while locking potential brain rhythms. Vibratory stimulation may potentially be in phase with natural oscillations. However, due to complexity and temporal variability of the EEG signals, matching with spontaneous oscillations of the human body is a challenging problem.

SUMMARY

The present invention aims at solving the technical problems to overcome the defects in the prior art and to provide a brain-computer interface method and system based on real-time closed loop vibration stimulation enhancement by aiming at the characteristic problems of nonlinear, nonstable, non-gaussian processes and the like of an electroencephalogram signal per se, thus improving a signal-to-noise ratio of a brain-computer interface system and enhancing a brain source signal.

The present invention solves the above technical problems specifically by the following technical solution:

A brain-computer interface method based on real-time closed loop vibration stimulation enhancement includes the following steps:

displaying and providing a motor imagery task to a subject, and collecting a digital electroencephalogram signal of the subject generated during motor imagery;

reading the collected digital electroencephalogram signal, judging whether a preset time period is exceeded or not, intercepting the digital electroencephalogram signal in the preset time period if YES, and continuously reading the collected digital electroencephalogram signal if NO;

after band-pass filtering is performed on the intercepted digital electroencephalogram signal in the preset time period, obtaining time-frequency characteristics of the digital electroencephalogram signal of the period through calculation by fast Fourier transform, and extracting a frequency value with highest frequency energy as its main frequency; obtaining an instantaneous phase of the digital electroencephalogram signal of the period through calculation by Hilbert transform on the digital electroencephalogram signal subjected to band-pass filtering; generating predicted sine waves by respectively using the main frequency and the instantaneous phase of the digital electroencephalogram signal of the period as a frequency and an initial phase of sine waves, and predicting and obtaining real-time phase information at the current moment according to the predicted sine waves; and judging whether the real-time phase is in a vibration stimulation application phase interval or not according to the predicted and obtained real-time phase information at the current moment, generating and outputting a control instruction according to the judging result, and controlling a vibration motor to vibrate and to stimulate a sensory channel of the subject according to the control instruction.

Further, as a preferable technical solution of the present invention, the motor imagery task in the method includes a left-hand or right-hand motor imagery action.

Further, as a preferable technical solution of the present invention, in the method, the intercepted digital electroencephalogram signal in the preset time period is subjected to a waveband band-pass filtering.

Further, as a preferable technical solution of the present invention, for obtaining the instantaneous phase of the digital electroencephalogram signal of the period through calculation by Hilbert transform in the method, the following formulas are used:

$$y_{(t)} = p \cdot \frac{1}{\pi} \cdot v \cdot \int_{-\infty}^{+\infty} \frac{x_{(t)}}{t-\tau} d\tau; \text{ and}$$

$$\theta_x(t) = \tan^{-1} \frac{y(t)}{x(t)},$$

wherein y(t) is a digital electroencephalogram signal after Hilbert transform is performed on x(t); x(t) is the digital electroencephalogram signal of the period after the band-pass filtering; p and v are integrals in the Cauchy principal value sense; and $\theta_x(t)$ is an instantaneous phase at a moment t.

Further, as a preferable technical solution of the present invention, the predicted sine wave $f_s$ generated in the method is specifically:

$$f_s = \sin(2 \cdot \pi \cdot f_{main} \cdot t_f + \theta x(t) + \frac{\pi}{2}),$$

wherein $f_{main}$ is a main frequency of the intercepted digital electroencephalogram signal of the preset time period; $t_f$ is a length of a predicted waveform, and $\theta_x(t)$ is an instantaneous phase at the moment t.

The brain-computer interface system based on real-time closed loop vibration stimulation enhancement provided by the present invention includes:

a human-computer interaction module, configured to display and provide a motor imagery task to a subject;

an electroencephalogram signal collection module, configured to collect a digital electroencephalogram signal generated during motor imagery of the subject;

a real-time phase prediction module, configured to read the collected digital electroencephalogram signal, judge whether the preset time period is exceeded or not, intercept the digital electroencephalogram signal in the preset time period if YES, and continuously read the collected digital electroencephalogram signal if NO; and configured to obtain time-frequency characteristics of the digital electroencephalogram signal of the period through calculation by fast Fourier transform after performing band-pass filtering on the intercepted digital electroencephalogram signal in the preset time period, extract a frequency value with highest frequency energy in the time-frequency characteristics as its main frequency, obtain an instantaneous phase of the digital electroencephalogram signal of the period through calculation by Hilbert transform, generate predicted sine waves by respectively using the main frequency and the instantaneous phase of the digital electroencephalogram signal of the period as a frequency and an initial phase of sine waves, and predict and obtain real-time phase information at the current moment according to the predicted sine waves;

an electroencephalogram signal analysis module, configured to judge whether the real-time phase is in a vibration stimulation application phase interval or not according to the predicted and obtained real-time phase information at the current moment, and generate and output a control instruction according to the judging result; and a vibration stimulation feedback module, configured to control a vibration motor to vibrate and to stimulate a sensory channel of the subject according to the control instruction output by the electroencephalogram signal analysis module.

Further, as a preferable technical solution of the present invention, the electroencephalogram signal collection module includes an electroencephalogram cap, an electroencephalogram signal amplifier, a low-pass and band-stop filter, an analog-to-digital conversion module and a communication module in sequential connection.

Further, as a preferable technical solution of the present invention, the real-time phase prediction module uses a band-pass filter to perform band-pass filtering on the digital electroencephalogram signal in the preset time period.

Further, as a preferable technical solution of the present invention, the band-pass filter adopts a ten-order oval infinite impulse response filter.

Further, as a preferable technical solution of the present invention, the vibration stimulation feedback module sets different vibration frequencies to act on the left hand and the right hand according to the control instruction.

By using the above technical solution, the present invention can achieve the following technical effects:

The method and system of the present invention achieve a real-time closed loop vibration stimulation effect so as to enhance a signal-to-noise ratio of the electroencephalogram signal and improve a decoding rate of the motor imagery task by guiding a subject to execute a motor imagery task via display, generating predicted sine waves by using the data period time-frequency characteristics of the collected electroencephalogram signals, then predicting the real-time electroencephalogram signal phase information on the basis of the predicted sine waves, and controlling the vibration motor to apply vibration stimulation on the fingertip of a person by using the predicted instantaneous phase information. The present invention can feedback, regulate and control the electroencephalogram rhythm through vibration stimulation. A signal-to-noise ratio of the brain-computer interface system is improved. A new scheme is provided for enhancing a brain source signal. The recognition rate of the motor imagery signal is enhanced. A "BCI blind" phenomenon is reduced. Therefore, the communication between the user and the outside is more effective, more convenient and faster.

Therefore, the present invention can improve real-time performance of vibration stimulation. The stimulation effect is maximized by concentrating the stimulation on the optimum phase for enhancing the electroencephalogram signal and ensuring the repeating in a plurality of cycles. The decoding rate of the motor imagery task is improved. Differences of the brain-computer interface between individuals are reduced. Compared with a traditional open-loop continuous stimulation method, such a system can realize vibration control at lower power demand and higher specificity, and can reduce tolerance and rebounding risks.

DETAILED DESCRIPTION

Implementations of the present invention are described below with reference to the accompanying drawings of this specification.

Figure 1:
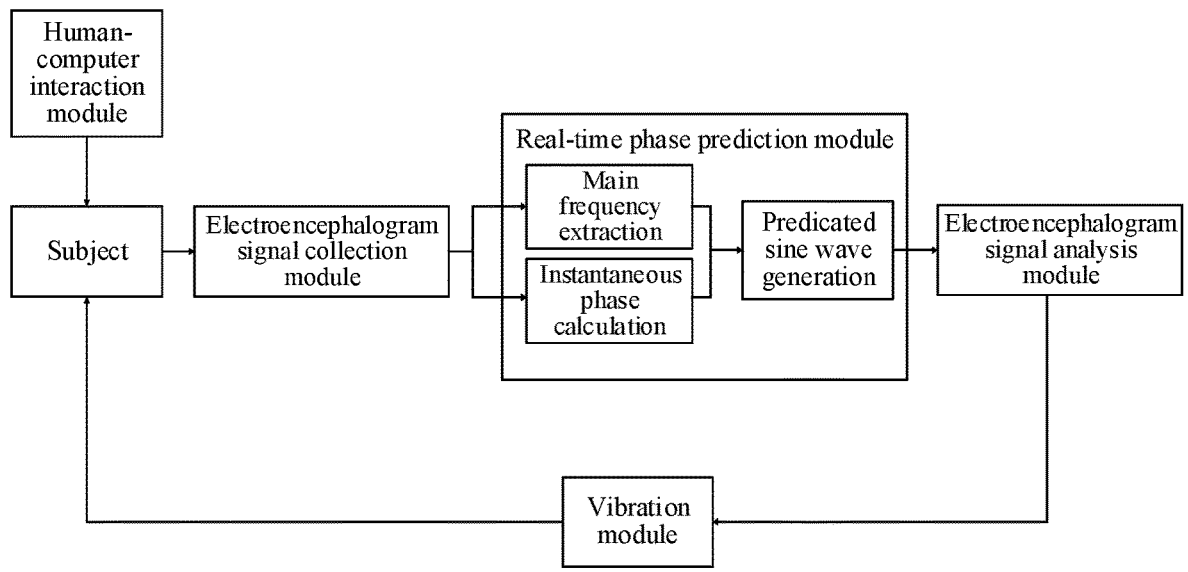
FIG. 1 is a schematic structure diagram of a brain-computer interface system based on real-time closed-loop vibration stimulation enhancement.
Figure 2:
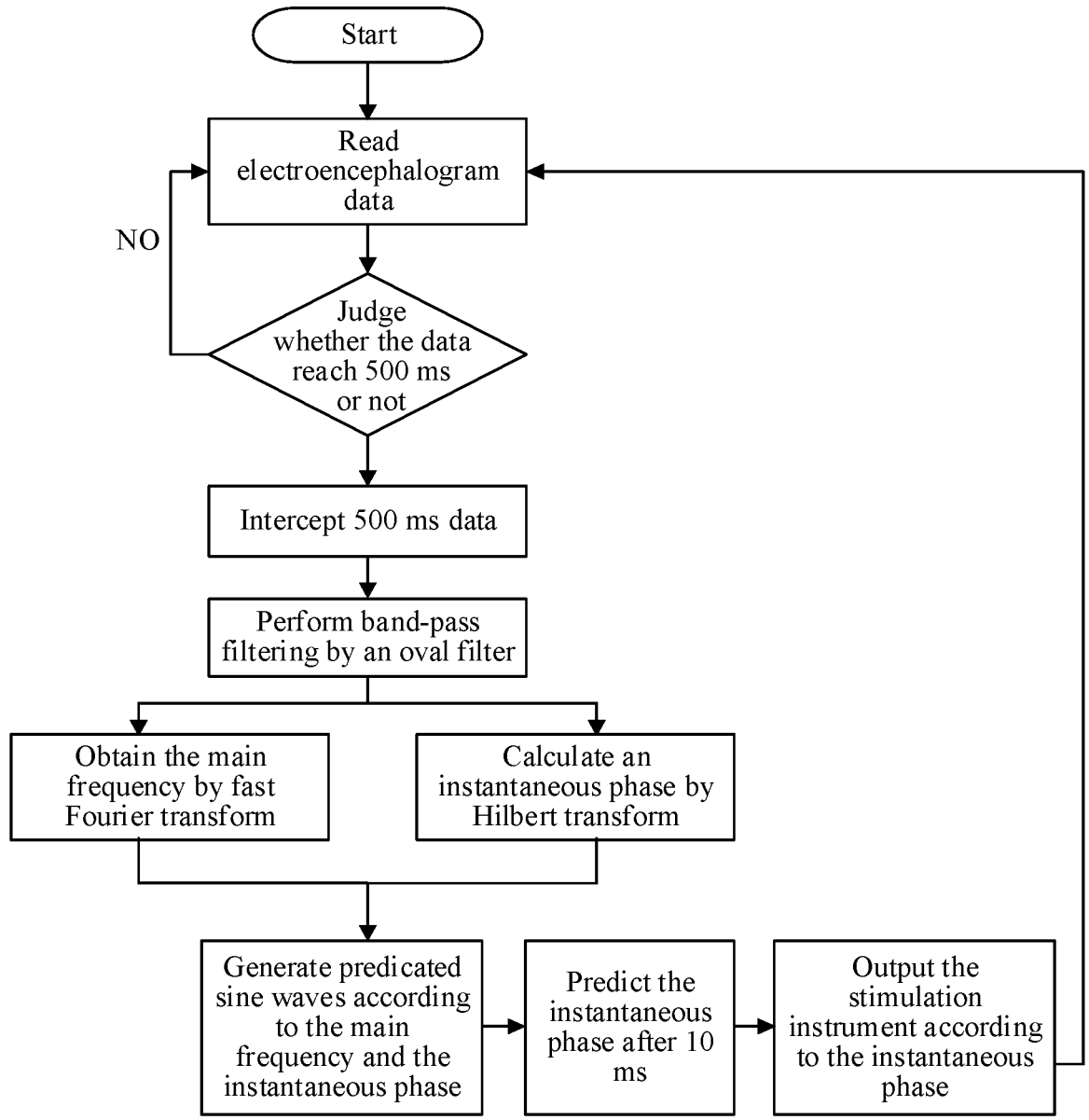
FIG. 2 is a real-time phase prediction flow diagram in a method of the present invention.

As shown in FIG. 1, the present invention designs a brain-computer interface system based on real-time closed-loop vibration stimulation enhancement. The system mainly includes: a human-computer interaction module, an electroencephalogram signal collection module, a real-time phase prediction module, an electroencephalogram signal analysis module and a vibration stimulation feedback module. An output end of the electroencephalogram signal collection module is connected with an input end of the real-time phase prediction module. An output end of the real-time phase prediction module is connected with an input end of the electroencephalogram signal analysis module. An output end of the electroencephalogram signal analysis module is connected with the vibration stimulation feedback module. The vibration stimulation feedback module directly acts on the body of a subject, and acts on the left and right hands of the subject in the present embodiment.

The human-computer interaction module consists of a display screen displaying a motor imagery task on a screen, and is configured to display and provide the motor imagery task to the subject and guide the subject to complete the left-hand or right-hand motor imagery task through a visual channel.

The electroencephalogram signal collection module is configured to collect a digital electroencephalogram signal of the subject generated during motor imagery, and mainly includes an electroencephalogram cap, an electroencephalogram signal amplifier, a low-pass and band-stop filter, an analog-to-digital conversion module and a communication module in sequential connection. The electroencephalogram cap is worn on the head of the subject, and collects the electroencephalogram signal of the subject generated during motor imagery. The digital electroencephalogram signal is obtained sequentially through amplification by the electroencephalogram signal amplifier, low-pass filtering by the low-pass and band-stop filter and the analog-to-digital conversion by the analog-to-digital conversion module. The digital electroencephalogram signal is transmitted to the real-time phase prediction module through the communication module.

The real-time phase prediction module is configured to receive the digital electroencephalogram signal transmitted by the electroencephalogram signal collection module through a USB interface, read the collected digital electroencephalogram signal, judge whether a preset time period is exceeded or not, intercept the digital electroencephalogram signal in the preset time period if YES, and continuously read the collected digital electroencephalogram signal if NO; and is configured to obtain time-frequency characteristics of the digital electroencephalogram signal of the period through calculation by fast Fourier transform after performing band-pass filtering on the intercepted digital electroencephalogram signal in the preset time period, extract a frequency value with highest frequency energy in the time-frequency characteristics as its main frequency, obtain an instantaneous phase of the digital electroencephalogram signal of the period through calculation by Hilbert transform, generate predicted sine waves by respectively using the main frequency and the instantaneous phase of the digital electroencephalogram signal of the period as a frequency and an initial phase of sine waves, and predict and obtain real-time phase information at the current moment according to the predicted sine waves to realize the instantaneous phase prediction on the real-time electroencephalogram signal.

The electroencephalogram signal analysis module is configured to judge whether the real-time phase is in a vibration stimulation application phase interval or not according to the real-time phase information predicted and obtained by the real-time phase prediction module at the current moment, and generate and output a control instruction according to the judging result.

The vibration stimulation feedback module is configured to control a vibration motor to vibrate and to stimulate a sensory channel of the subject according to the control instruction output by the electroencephalogram signal analysis module, stimulate the fingertip of the subject to further influence the sensory channel of the subject, and regulate the electroencephalogram signal rhythm.

Preferably, the digital electroencephalogram signal includes an imagery fisting motion signal. The real-time phase prediction module of the system of the present invention adopts the band-pass filter to perform band-pass filtering on the digital electroencephalogram signal in the preset time period. The frequency band of the band-pass filtering is a brain activity $\alpha$ frequency band. Further, the band-pass filter adopts a ten-order oval infinite impulse response filter. That is, 500 ms is used as a data segment for real-time analysis. Firstly, the electroencephalogram signal data segment is subjected to band-pass filtering by the ten-order oval infinite impulse response filter to obtain the required digital electroencephalogram signal at an $\alpha$ frequency band and in a range of 8-12 hz. The passband ripple is set to be 0.5 dB. The stopband attenuation is set to be 40 dB. The selected data fragment is short, so the order number will be limited if a finite impulse response (FIR) filter is adopted. An infinite impulse response (IIR) filter is adopted.

Additionally, the vibration stimulation feedback module in the system of the present invention can set different vibration frequencies according to the control instruction to act on the left hand and the right hand. For example, a vibration stimulation signal set in the vibration stimulation module and acting on the left hand is sine waves at a vibration frequency of 22 hz, and a vibration stimulation signal acting on the right hand is sine waves at a vibration frequency of 26 hz. The human body sensory system has different sensitive degrees on the left and the right, so the optimum stimulation effect can be generated in an auxiliary way by setting different vibration frequencies.

The present invention further provides a brain-computer interface method based on real-time closed-loop vibration stimulation enhancement. The method is used for signal processing of the above system, and specifically includes the following steps:

Step 1: The human-computer interaction module displays and provides the motor imagery task to a subject. The motor imagery task may include a left-hand or right-hand motor imagery action. Stimulation displayed in a display in the human-computer interaction module includes three modes, specifically including:

(1) a white cross mark occurs in the right center of a screen, and the subject is relaxed and does not perform imagery;

(2) a red arrow occurs at a left end of the white cross mark, and the subject executes a left-hand motor imagery task; and (3) a red arrow occurs at a right end of the white cross mark, and the subject executes a right-hand motor imagery task.

While the arrow occurs, the real-time vibration stimulation module is activated. The vibration stimulation module is mainly configured to generate stimulation feedback according to the electroencephalogram signal obtained in real time, thus achieving an effect of enhancing the electroencephalogram signal.

Then, the subject sits on a comfortable chair according to requirements, and wears a 64-lead electroencephalogram cap on the head. A distance between the two eyes and the display is about one meter. The left-hand or right-hand fisting action is imaged according to a pointing direction of the arrow displayed on the display. The real-time electroencephalogram signal data of the user is obtained through the 64-lead electroencephalogram collection cap in the electroencephalogram signal collection module. Sequentially through processing and collection by each component, the digital electroencephalogram signal data generated during motor imagery is obtained.

Step 2: The real-time phase prediction module executes a real-time electroencephalogram signal phase prediction algorithm while the motor imagery task is started. As shown in the figure, a specific process is as follows:

Firstly, the real-time phase prediction module reads the collected digital electroencephalogram signal and judges whether the preset time period is exceeded or not. For example, whether 500 ms is exceeded or not. If 500 ms is exceeded, the digital electroencephalogram signal in the preset time period 500 ms is intercepted for analysis and prediction. If 500 ms is not exceeded, the collected digital electroencephalogram signal is continuously read.

Then, the real-time phase prediction module performs an analysis and prediction process:

The intercepted digital electroencephalogram signal in the preset time period 500 ms is subjected to band-pass filtering to obtain a specific occurrence frequency band of an ERD phenomenon under the motor imagery task, such as the α wave band. The range is 8-12 hz.

For the digital electroencephalogram signal data subjected to band-pass filtering, the time-frequency characteristics of the digital electroencephalogram signal of the period is obtained through calculation by fast Fourier transform, and a frequency value with highest frequency energy is extracted to be used as the main frequency of the digital electroencephalogram signal of the period. In the present embodiment, the frequency value with the highest frequency energy in the signal period is extracted to be used as the main frequency of the signal of the period.

For the digital electroencephalogram signal subjected to band-pass filtering, an instantaneous phase of the digital electroencephalogram signal x(t) of the period is obtained through calculation by Hilbert transform. For the instantaneous phase extraction, through calculation by Hilbert transform, the digital electroencephalogram signal y(t) after Hilbert transform is performed on x(t) is obtained. The following formula is used:

$$y_{(t)} = p \cdot \frac{1}{\pi} \cdot v \cdot \int_{-\infty}^{+\infty} \frac{x_{(t)}}{t - \tau} d\tau.$$

The instantaneous phase at the moment t may be calculated through the following formula:

$$\theta_x(t) = \tan^{-1} \frac{y(t)}{x(t)},$$

wherein $\theta_x(t)$ is an instantaneous phase at the moment t; x(t) is the digital electroencephalogram signal of the period after the band-pass filtering; and p and v are integrals in the Cauchy principal value sense.

Finally, the predicted sine waves are generated by respectively using the main frequency and the instantaneous phase of the digital electroencephalogram signal of the period as a frequency and an initial phase of sine waves. The prediction on the real-time phase is realized according to the real-time phase information predicted and obtained by the predicted sine waves. The sine wave function formula is as follows:

$$f_s = \sin\left(2 \cdot \pi \cdot f_{main} \cdot t_f + \theta x(t) + \frac{\pi}{2}\right),$$

wherein $f_s$ is predicted sine waves; $f_{main}$ is the main frequency of the intercepted digital electroencephalogram signal of the preset time period; $t_f$ is a length of a predicted waveform, is set to be 50 ms herein, and may be determined according to the time difference of the selected current time point and the time point of obtaining the instantaneous phase of the electroencephalogram signal; and $\theta_x(t)$ is an instantaneous phase at the moment t.

In the above, the instantaneous phase at a 480 ms position in the 500 ms electroencephalogram signal data is obtained through Hilbert transform, i.e., t=480 ms. The main frequency $f_{main}$ of the data fragment is obtained through calculation by fast Fourier transform. Through these parameters, a sine wave functional expression can be listed to obtain the precise predicted sine waves. The length $t_f$ of the predicted waveform is set to be one-tenth of a length of a reference signal, i.e., 50 ms. A principle is that the electroencephalogram signal is a nonlinear and instable signal, and therefore, 500 ms of data is extracted in per 50 ms fragment for prediction, so as to improve the prediction accuracy.

Step 3: The electroencephalogram signal analysis module judges whether the real-time phase is in a vibration stimulation application phase interval or not according to the real-time phase information predicted and obtained by the real-time phase prediction module at the current moment t. If the judging result is that the real-time phase is in the phase interval, a control instruction is generated and output. The vibration stimulation feedback module controls a vibration motor to vibrate and to stimulate a sensory channel of the subject according to the control instruction. Otherwise, if the judging result is that the real-time phase is not in the phase interval, the control instruction is not output, and the vibration stimulation does not need to be generated.

Figure 3:
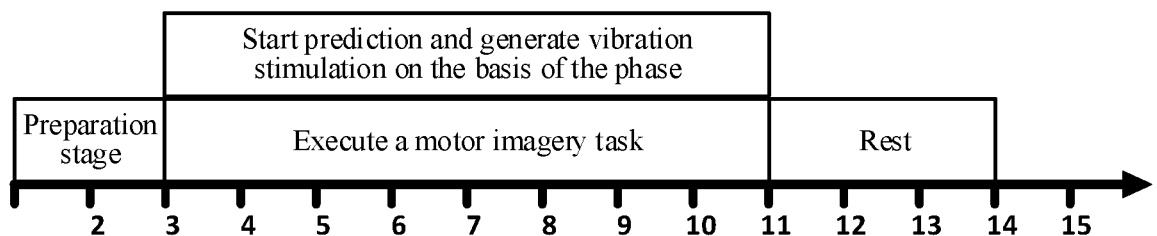
FIG. 3 is a schematic diagram of a motor imagery experimental paradigm based on real-time closed-loop stimulation feedback of the present invention.

The present invention uses the above method. Its test result is as shown in FIG. 3. About 3 ms is needed from the generation of the electroencephalogram signal, to the recording by the electroencephalogram cap, and then to the entering of the real-time phase prediction module through an amplifier and USB transmission. About 5 ms is needed for a computer to execute a prediction algorithm for data processing. About 2 ms is needed for obtaining the instantaneous phase value and converting the instantaneous phase value into an instruction to control the vibration motor to vibrate. Therefore, the 30$^{th}$ ms position of the predicted sine waves may be approximately regarded as the electroencephalogram signal of the current time point. The instantaneous phase at a 30 ms position is taken to be used as a point for the vibration motor to control a triggering signal, thus achieving the goal of stimulation based on the real-time phase.

Based on the above, the present invention designs the brain-computer interface method and system capable of performing fingertip vibration stimulation so as to enhance the decoding rate of the motor imagery task on the basis of the real-time phase of the electroencephalogram signal. By aiming at the problems of low decoding rate, too great individual differences, "BCI blind" phenomenon and the like of the existing motor imagery brain-computer interface, a method for enhancing the electroencephalogram signal is designed. Compared with the past continuous closed-loop vibration stimulation, the present invention achieves the maximum stimulation effect through cumulative effect by concentrating the stimulation on the optimum phase for enhancing the electroencephalogram signal and ensuring the repeating in a plurality of cycles. Therefore, the vibration control can be realized at lower power demand and higher specificity. Additionally, the tolerance and rebounding risks can be reduced. By feeding back, regulating and controlling the electroencephalogram rhythm through vibration stimulation, the present invention improves a signal-to-noise ratio of the brain-computer interface system, and enhances the recognition rate of a motor imagery signal.

The implementations of the present invention are described above in detail with reference to the accompanying drawings, but the present invention is not limited to the implementations described above. A person of ordinary skill in the art may make various variations without departing from the spirit of the present invention.

What is claimed is:

1. A brain-computer interface method based on real-time closed loop vibration stimulation enhancement, comprising the following steps:

displaying and providing a motor imagery task to a subject, and collecting a digital electroencephalogram signal of the subject generated during motor imagery;

reading the collected digital electroencephalogram signal, judging whether a preset time period is exceeded or not, intercepting the digital electroencephalogram signal in the preset time period if YES, and continuously reading the collected digital electroencephalogram signal if NO;

after band-pass filtering is performed on the intercepted digital electroencephalogram signal in the preset time period, obtaining time-frequency characteristics of the digital electroencephalogram signal of the period through calculation by fast Fourier transform, and extracting a frequency value with highest frequency energy as a main frequency; obtaining an instantaneous phase of the digital electroencephalogram signal of the period through calculation by Hilbert transform on the digital electroencephalogram signal subjected to band-pass filtering; generating predicted sine waves by respectively using the main frequency and the instantaneous phase of the digital electroencephalogram signal of the period as a frequency and an initial phase of sine waves, and predicting and obtaining real-time phase information at the current moment according to the predicted sine waves; and judging whether the real-time phase is in a vibration stimulation application phase interval or not according to the predicted and obtained real-time phase information at the current moment, generating and outputting a control instruction according to the judging result, and controlling a vibration motor to vibrate and to stimulate a sensory channel of the subject according to the control instruction.

2. The brain-computer interface method based on real-time closed loop vibration stimulation enhancement according to claim 1, wherein the motor imagery task in the method comprises a left-hand or right-hand motor imagery action.

3. The brain-computer interface method based on real-time closed loop vibration stimulation enhancement according to claim 1, wherein in the method, the intercepted digital electroencephalogram signal in the preset time period is subjected to α waveband band-pass filtering.

4. The brain-computer interface method based on real-time closed loop vibration stimulation enhancement according to claim 1, wherein for obtaining the instantaneous phase of the digital electroencephalogram signal through calculation by Hilbert transform in the method, the following formulas are used:

$$y_{(t)} = p \cdot \frac{1}{\pi} \cdot v \cdot \int_{-\infty}^{+\infty} \frac{x_{(t)}}{t - \tau} d\tau; \text{ and}$$

$$\theta_x(t) = \tan^{-1} \frac{y(t)}{x(t)},$$

wherein y(t) is a digital electroencephalogram signal after Hilbert transform is performed on x(t); x(t) is the digital electroencephalogram signal after the band-pass filtering; p and v are integrals in the Cauchy principal value sense; and θ$_x$(t) is an instantaneous phase at a moment t.

5. The brain-computer interface method based on real-time closed loop vibration stimulation enhancement according to claim 1, wherein the predicted sine wave f$_s$ generated in the method is specifically:

$$f_s = \sin\left(2 \cdot \pi \cdot f_{main} \cdot t_f + \theta x(t) + \frac{\pi}{2}\right),$$

wherein f$_{main}$ is a main frequency of the intercepted digital electroencephalogram signal of the preset time period; t$_f$ is a length of a predicted waveform, and θ$_x$(t) is an instantaneous phase at the moment t.

6. A brain-computer interface system based on real-time closed loop vibration stimulation enhancement, comprising:

a human-computer interaction module, configured to display and provide a motor imagery task to a subject;

an electroencephalogram signal collection module, configured to collect a digital electroencephalogram signal generated during motor imagery of the subject;

a real-time phase prediction module, configured to read the collected digital electroencephalogram signal, judge whether the preset time period is exceeded or not, intercept the digital electroencephalogram signal in the preset time period if YES, and continuously read the collected digital electroencephalogram signal if NO; and configured to obtain time-frequency characteristics of the digital electroencephalogram signal of the period through calculation by fast Fourier transform after performing band-pass filtering on the intercepted digital electroencephalogram signal in the preset time period, extract a frequency value with highest frequency energy in the time-frequency characteristics as its main frequency, obtain an instantaneous phase of the digital electroencephalogram signal of the period through calculation by Hilbert transform, generate predicted sine waves by respectively using the main frequency and the instantaneous phase of the digital electroencephalogram signal of the period as a frequency and an initial phase of sine waves, and predict and obtain real-time phase information at the current moment according to the predicted sine waves; and a controller that is configured to function as:

an electroencephalogram signal analysis module, configured to judge whether the real-time phase is in a vibration stimulation application phase interval or not according to the predicted and obtained real-time phase information at the current moment, and generate and output a control instruction according to the judging result; and a vibration stimulation feedback module, configured to control a vibration motor to vibrate and to stimulate a sensory channel of the subject according to the control instruction output by the electroencephalogram signal analysis module.

7. The brain-computer interface method based on real-time closed loop vibration stimulation enhancement according to claim 6, wherein the real-time phase prediction module uses a band-pass filter to perform band-pass filtering on the digital electroencephalogram signal in the preset time period.

8. The brain-computer interface method based on real-time closed loop vibration stimulation enhancement according to claim 7, wherein the band-pass filter adopts a ten-order oval infinite impulse response filter.

9. The brain-computer interface method based on real-time closed loop vibration stimulation enhancement according to claim 6, wherein the electroencephalogram signal collection module comprises an electroencephalogram cap, an electroencephalogram signal amplifier, a low-pass and band-stop filter, an analog-to-digital conversion module and a communication module in sequential connection.

10. The brain-computer interface method based on real-time closed loop vibration stimulation enhancement according to claim 6, wherein the vibration stimulation feedback module sets different vibration frequencies to act on the left hand and the right hand according to the control instruction.

* * * * *